US007056517B2

(12) United States Patent
Smith et al.

(10) Patent No.: US 7,056,517 B2
(45) Date of Patent: *Jun. 6, 2006

(54) GLUCOSYLTRANSFERASE IMMUNOGENS (75) Inventors: Daniel J. Smith, Natick, MA (US); Martin A. Taubman, Newtonville, MA (US)

(73) Assignee: The Forsyth Institute, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/797,302

(22) Filed: Mar. 9, 2004

(65) Prior Publication Data
US 2005/0026271 A1 Feb. 3, 2005

Related U.S. Application Data (63) Continuation-in-part of application No. 10/383,930, filed on Mar. 7, 2003, which is a continuation-in-part of application No. 09/290,049, filed on Apr. 12, 1999, now Pat. No. 6,827,936.

(60) Provisional application No. 60/081,550, filed on Apr. 13, 1998, provisional application No. 60/402,483, filed on Aug. 8, 2002, provisional application No. 60/363,209, filed on Mar. 7, 2002, provisional application No. 60/115,142, filed on Jan. 8, 1999.

(51) Int. Cl.
| A61K 39/02 | (2006.01) |
| A61K 39/38 | (2006.01) |
| A61K 38/00 | (2006.01) |
| C07H 21/04 | (2006.01) |

(52) U.S. Cl. ............ 424/190.1; 424/9.1; 424/9.2; 424/184.1; 424/185.1; 424/193.1; 424/197.11; 424/234.1; 424/244.1; 435/69.1; 435/183; 435/193; 435/253.4; 530/300; 530/350

(58) Field of Classification Search ........... 424/9.1, 424/9.2, 184.1, 185.1, 190.1, 193.1, 197.11, 424/234.1, 244.1; 435/69.1, 183, 193, 253.4; 530/300, 350
See application file for complete search history.

(56) References Cited

U.S. PATENT DOCUMENTS

| 4,150,116 A | | 4/1979 | Taubman et al. ............ 424/88 |
| 4,250,262 A | | 2/1981 | Taubman et al. ........... 435/193 |
| 4,438,200 A | | 3/1984 | Taubman et al. ........... 435/193 |
| 5,019,400 A | * | 5/1991 | Gombotz et al. ........... 424/497 |
| 5,223,409 A | | 6/1993 | Ladner et al. ............. 435/69.7 |
| 5,686,075 A | | 11/1997 | Taubman et al. ...... 424/197.11 |

FOREIGN PATENT DOCUMENTS

| WO | WO 90/02809 | 3/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 99/07828 | 2/1999 |

OTHER PUBLICATIONS

Banas, et al., *Infect. Immun.*, 58(3):667-673 (1990).
Banas, et al., *FEMS Microbiol. Lett.*, 154:289-292 (1997).
Chia, et al., *Infect. Immun.*, 61(11):4689-4695 (1993).
Chia, et al., *Infect. Immun.*, 69(4):2493-2501 (2001).
Cole, et al., *Monoclonal Antibodies and Cancer Therapy*, pp. 77-96 (1985).
Dertzbaugh, et al., *Infect. Immun.*, 58(6):1509-1513 (1990).
Dertzbaugh, et al., *Infect. Immun.*, 58(1):70-79 (1990).
Devulapalle, et al., *Protein Sci.*, 6:2489-2493 (1997).
Ferretti, et al., *J. Bacteriol.*, 169(9):4271-4278 (1987).
Ferretti, et al., *Infect. Immun.*, 56(6):1585-1588 (1988).
Fuchs, et al., *Biotechnology*, 9:1369-1372 (1991).
Funane, et al., *Biochem.*, 32:13696-13702 (1993).
Furst, et al., *Nucleic Acids Res.*, 17(16):6274 (1989).
Galfre, et al., *Nature*, 266(5602):550-552 (1977).
GenBank Accession No. AY046410 (2001).
GenBank Accession No. AY046411 (2001).
GenBank Accession No. AY046412 (2001).
GenBank Accession No. AY046413 (2001).
GenBank Accession No. AY046414 (2001).
Griffiths, et al., *EMBO J.*, 12(2):725-734 (1993).
Hamada, et al., *Microbiol. Rev.*, 44(2):331-384 (1980).
Hay, et al., *Hum. Antibod. Hybridomas*, 3:81-85 (1992).
Higgins, et al., *CABIOS Communications*, 5(2):151-153 (1989).
Hopp, et al., *Proc. Natl. Acad. Sci. USA*, 78(6):3824-3828 (1981).
Huse, et al., *Science*, 246:1275-1281 (1989).
Jenkins, et al., *FEBS Lett.*, 362:281-285 (1995).
Jespergaard, et al., *Infect. Immun.*, 67(2):810-816 (1999).

(Continued)

*Primary Examiner*—Rodney P Swartz
(74) *Attorney, Agent, or Firm*—Mintz, Levin, Cohn, Ferris, Glovsky and Popeo, P.C.; Ingrid A. Beattie (57) ABSTRACT

Vaccine compositions and immunogenic compositions are described which are glucosyltransferase subunit vaccines for dental caries and which contain at least one peptide which corresponds to a sequence of glucosyltransferase containing aspartate 413, an equivalent of aspartate 413, aspartate 451, an equivalent of aspartate 451, aspartate 562, an equivalent of aspartate 562, aspartate 567, an equivalent of aspartate 567, histidine 561, an equivalent of histidine 561, tryptophan 491, an equivalent of tryptophan 491, glutamate 489, an equivalent of glutamate 489, arginine 449, an equivalent of arginine 449, or combinations thereof. These subunit vaccines elicit antibodies which protect an immunized mammal from dental caries. Methods of provoking an immune response to intact glucosyltransferase are also described.

4 Claims, 2 Drawing Sheets

OTHER PUBLICATIONS

Jespergaard, et al., *Infect. Immun.*, 67(12):6543-6549 (1999).
Keyes, et al., *Arch. Oral Biol.*, 9:377-400 (1964).
Köhler, et al., *Nature*, 266(5602):495-497 (1975).
Kolenbrander, P.E., *Annu. Rev. Microbiol.*, 54:413-437 (2000).
Kuramitsu, et al., *Archs. Oral Biol.*, 23(8):691-696 (1978).
Lerner, E.A., *Yale J. Biol. Med.*, 54(5):387-402 (1981).
Loo, et al., *J. Bacteriol.*, 182(5):1374-1382 (2000).
Ma, et al., *Eur. J. Immunol.*, 24:131-138 (1994).
MacGregor, et al., *FEBS Lett.*, 378:263-266 (1996).
Matsuura, et al., *J. Biochem.*, 95:697-702 (1984).
Mattos-Graner, et al., *J. Dent. Res.*, 79(6):1371-1377 (2000).
Mattos-Graner, et al., *Infect. Immun.*, 69(11):6931-6941 (2001).
Merrifield, R.B., *Synthesis of a Tetrapeptide*, 85:2149-2154 (1963).
Mooser, et al., *J. Dental Res.*, Abstract 1729, 69:325 (1990).
Mooser, et al., *J. Biol. Chem.*, 266(14):8916-8922 (1991).
Navarre, et al., *Mol. Microbiol.*, 14(1):115-121 (1994).
Reinscheid, et al., *J. Bacteriol.*, 183(40:1175-1183 (2001).
Russell, R.R.B., *J. Gen. Microbiol.*, 112:197-201 (1979).
Russell, et al., *J. Dental Res.*, 67(3):543-547 (1988).
Sato, et al., *Infect. Immun.*, 65(2):668-675 (1997).
Schubert, et al., *Arch. Microbiol.*, 173(1):21-28 (2000).
Shimamura, et al., *J. Bacteriol.*, 176(16):4845-4850 (1994).
Shiroza, et al., *J. Bacteriol.*, 169:4263-4270 (1987).
Smith, et al., *Infect. Immun.*, 21(3):843-851 (1978).
Smith, et al., *Infect. Immun.*, 23(2):446-452 (1979).
Smith, et al., *Infect. Immun.*, 26(1):82-89 (1979).
Smith, et al., *Infect. Immun.*, 28(2):441-450 (1980).
Smith, et al., *Archs. Oral Biol.*, 26:871-878 (1981).
Smith, et al., *Infect. Immun.*, 37(2):656-661(1982).
Smith, et al., *Infect. Immun.*, 42(1):156-162 (1983).
Smith, et al., *Infect. Immun.*, 55(11):2562-2569 (1987).
Smith, et al., *Oral Microbiol. Immun.*, 5(2):57-62 (1990).
Smith, et al., *J. Clin. Immunol.*, 10(5):273-281 (1990).
Smith, et al., *Infect. Immun.*, 61(7):2899-2905 (1993).
Smith, et al., *Oral Microbiol. Immun.*, 13(5):278-285 (1998).
Smith, et al., *Infect. Immun.*, 62(6):2545-2552 (1994).
Smith, et al., *Infect. Immun.*, 62(12):5470-5476 (1994).
Smith, et al., *Oral Micro Immunol.*, 9:65-69 (1994).
Smith, et al., *J. Dental Res.*, Abstract 818, 77:734 (1998).
Smith, et al., *Infect. Immun.*, 67(5):2638-2642 (1999).
Smith, et al., *J. Dental Res.*, 78:422 (1999).
Smith, et al., *Oral Microbiol. Immunol.*, 15:124-130 (2000).
Smith, et al., *Infect. Immun.*, 69(5):3135-3142 (2001).
Smith, et al., *Infect. Immun.*, 69(8):4767-4773 (2001).
Smith, et al., *Infect. Immun.*, 64(8):3069-3073 (1996).
Smith, et al., *Infect. Immun.*, 65(11):4424-4430 (1997).
Socransky, et al., *J. Clin. Microbiol.*, 22(2):303-305 (1985).
Søgaard, et al., *J. Biol. Chem.*, 268(30):22480-22484 (1993).
Svendsen, et al., *Lab. Anim. Sci.*, 45(1):89-93 (1995).
Tam, J.P., *Proc. Natl. Acad. Sci. USA*, 85(15):5409-5413 (1988).
Taubman, et al., *J. Immunol.*, 118(2):710-720 (1977).
Taubman, et al., *Recent Advances in Mucosal Immunity*, W. Strober, et al., eds. (NY Raven Press) pp. 371-382 (1982).
Taubman, et al., *Glucosyltransferase, Glucans, Sucrose and Dental Caries*, Doyle, et al., eds., Sp. Supp., *Chemical Senses*, pp. 249-258 (1983).
Taubman, et al., *J. Oral Pathol.*, 17:466-470 (1988).
Taubman, et al., *Infect. Immun.*, 63(8):3088-3093 (1995).
Taubman, et al., *J. Dent. Res.*, Abstract 2666, 76:347 (1997).
Taubman, et al., *Infect. Immun.*, 68(5):2698-2703 (2000).
Taubman, et al., *Infect. Immun.*, 69:4210-4216 (2001).
Tsumori, et al., *J. Bacteriol.*, 179(11):3391-3396 (1997).
Ueda, et al., *Gene*, 69:101-109 (1988).
U.S. non-published pending Appl. No. 09/562,328 by Andrew Lees, Martin A. Taubman and Daniel J. Smith, filed May 1, 2000.
U.S. Appl. No. 08/967,573 by Daniel J. Smith and Martin A. Taubman, filed Nov. 10, 1997.
Van Houte, et l., *J. Dent. Res.*, 68(3):451-459 (1989).

* cited by examiner

GLUCOSYLTRANSFERASE IMMUNOGENS

RELATED APPLICATIONS

This application is a continuation-in-part of U.S. application Ser. No. 09/290,049, filed Apr. 12, 1999, now issued as U.S. Pat. No. 6,827,936, which claims the benefit of U.S. provisional application Ser. No. 60/081,550 filed Apr. 13, 1998, and U.S. provisional application Ser. No. 60/115,142 filed Jan. 8, 1999; this application is also a continuation-in-part of U.S. application Ser. No. 10/383,930, filed Mar. 7, 2003, which claims the benefit of U.S. Provisional Application No. 60/363,209, filed Mar. 7, 2002 and U.S. Provisional Application No. 60/402,483, filed Aug. 8, 2002, the entire teachings of each are incorporated herein by reference.

GOVERNMENT FUNDING

Work described herein was supported by grant numbers DE-04733 and DE-06153 awarded by the National Institutes of Health, National Institute of Dental Research. The U.S. Government has certain rights in the invention.

BACKGROUND OF THE INVENTION

*Mutans streptococci* have been convincingly implicated in the initiation of dental caries in humans. The ability of these organisms to accumulate and colonize on the tooth surface has been associated with the synthesis of glucans from sucrose. Glucans are synthesized by constitutively secreted glucosyltransferase (GTF) enzymes. These enzymes have been considered as potential components of a dental caries vaccine because of their role in the pathogenicity of *Mutans streptococci*. However, vaccines based on intact GTF have a variety of disadvantages, such as the presence of inappropriate epitopes and excess molecular material that does not possess appropriate immunogenic features.

It is quite likely that protection against dental caries will involve functional inhibition of the catalytic and/or the glucan-binding activities of GTF. Epitopes associated with these functions would theoretically be primary targets for immunological attack, provided that the relevant sequences are located in molecular areas that are accessible to antibody. Subunit vaccines provide a method to block functional domains without inducing immunity to irrelevant or unwanted epitopes. It has been reported that synthetic peptide vaccines associated with catalytic or glucan-binding domains of GTF can protect rats from experimental dental caries (Taubman et al., *Infect. Immun.* 63:3088–3093 (1995)). One of the peptides that was successfully used as a vaccine (Smith et al., *Infect. Immun.* 62:5470–5476 (1994)) demonstrated a sequence containing an aspartic acid (aspartate 451 in *S. mutans* GTF-B) to which the glucosyl moiety of sucrose was covalently bound (Mooser et al., *J. Biol. Chem.* 266:8916–8922 (1991)).

SUMMARY OF THE INVENTION

Mutans streptococcal GTFs may contain several sequentially separated residues that, partly because of secondary structure constraints (e.g., $(\beta,\alpha)_8$ barrel domain), have important functions in GTF catalytic mechanisms. Peptides containing catalytically implicated aspartates (Asp 413/415 or Asp 451, based on the sequence numbering of *S. mutans* GTF B) each induced antibody that inhibited GTF activity and protected rats from experimental dental caries. Recent site-directed mutagenesis and comparative sequence studies have implicated these sequentially separated residues in the catalytic activity of mutans streptococcal glucosyltransferases (GTF). The immunogenicity and induction of GTF-inhibitory activity of synthetic peptides which contained putative catalytic regions that were associated with the $\beta_5$ (EAW peptide) and $\beta_7$ (HDS peptide) strand elements of the suggested $(\beta,\alpha)_8$ catalytic barrel domain of GTF were examined. Both peptides induced serum IgG and salivary IgA anti-peptide activity twenty one days after the second injection. Serum IgG antibody induced by HDS and EAW peptide constructs also showed significant reaction with *S. mutans* GTF. Antisera to each peptide construct also inhibited the ability of *S. mutans* GTF to synthesize glucan. These observations support the existence of catalytic subdomains containing glutamate and tryptophane (EAW) or aspartate and histidine (HDS) residues which have been suggested to be involved with the catalytic activity of GTF. Furthermore, the epitope(s) defined in these sequences have significant immunogenicity and can induce immune responses which interfere with GTF-mediated glucan synthesis.

This invention pertains to subunit vaccine compositions which elicit immune system responses in mammals to glucosyltransferase (GTF), an enzyme that is implicated in the formation of dental caries, or to subunits thereof. Rather than using intact GTF as an immunizing agent, the vaccine composition or immunogenic composition is prepared from particular immunogenic portions (subunits) of GTF.

The invention relates to vaccine compositions and immunogenic compositions comprising at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. In particular embodiments, the amino acid sequence is selected from the group consisting of 481-ANDHLSILEAWSDNDT-PYLHD (EAW peptide; SEQ ID NO: 1); and 552-VPSYS-FIRAHDSEVQDLIA (HDS peptide; SEQ ID NO: 2). These peptides are believed to be from the catalytic domain of GTF and have been shown to induce high levels of antibody that crossreact with intact GTF.

In another embodiment, the invention relates to a peptide having the amino acid sequence 1300-TGARTINGQLLY-FRANGVQVKG (GLB peptide; SEQ ID NO: 3); this sequence is believed to be from the glucan binding region of GTF.

In a particularly preferred embodiment, 2 or more of the peptides are present and arranged on a core matrix of 3 or more lysines.

The invention also relates to vaccine compositions and immunogenic compositions comprising at least two peptides covalently attached to a peptidyl core matrix, wherein each peptide consists essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. In a particular embodiment, the amino acid sequence is selected from the group consisting of the EAW peptide (ANDHLSILEAWSDNDTPYLHD; (SEQ ID NO: 1)) and the HDS peptide (VPSYSFIRAHDSEVQDLIA; (SEQ ID NO: 2)). In another embodiment, the peptide is the GLB peptide (TGARTINGQLLYFRANGVQVKG; (SEQ ID NO: 3)). In additional embodiments, the composition further comprises at least one additional immunologic component covalently attached to said peptidyl core matrix. For example, the additional immunologic component can be an immunogenic portion of a pathogen selected from the group consisting of diphtheria, pertussis, tetanus, measles and polio vaccines.

The invention also pertains to a method of provoking an immune response to glucosyltransferase in mammals comprising administering to a mammal at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, which is of sufficient length to raise an immune response in the mammal, thereby provoking said immune response. In a preferred embodiment, the immune response results in reduction of the colonization or accumulation of mutans streptococcal strains in the mammal to whom the peptide is administered.

The invention further pertains to a method of immunizing a mammal against dental caries comprising administering to the mammal at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in the mammal.

DETAILED DESCRIPTION OF THE INVENTION

The principal etiologic agents of dental caries are Mutans streptococci. These oral pathogens infect the oral cavity during early childhood and normally remain associated with the host's dentition for life. Mutans streptococci must colonize and then accumulate on the tooth surface in sufficient numbers to achieve dissolution of the enamel. After the initial colonization by Mutans streptococci on the tooth surface, the Mutans streptococci produce glucosyltransferase (GTF), an enzyme which catalyzes the synthesis of glucans from sucrose. In addition, S. mutans express cell surface proteins which serve as glucan binding sites. Glucans mediate much of the subsequent accumulation of Mutans streptococci on the tooth surface. This results in an increase in the numbers of potentially cariogenic bacteria in plaque. The metabolism of various saccharides by the accumulated bacterial mass results in excretion of significant amounts of lactic acid as a metabolic product, which causes demineralization when present in sufficient amount in close proximity to the tooth surface. This eventually results in a carious lesion (a cavity).

Recently, primary and secondary structural comparisons of glucosyltransferases with the alpha amylase superfamily have provided insights into the structure-function relationships of the GTF catalytic domain. Much of the catalytic activity of alpha amylases is contained in a $(\beta,\alpha)_8$ barrel element (Matsuura, et al., J. Biochem. 95:697–702 (1984)). Aspartates or glutamates at the C terminus of β strands (Dertzbaugh, et al., Infect. Immun. 58:70–79 (1990); Devulapalle, et al., Protein Science 6:2489–2493 (1997); Funane, et al., Biochem. 32:13696–13702 (1993)) have been specifically implicated in amylolytic activity and are invariant in these enzymes (Jenkins, et al., FEBS Lett. 362:281–285 (1995)). The overall homology between alpha amylases and GTF is low, except for a 50–60 amino acid sequence stretch near the middle of the GTF molecule (Ferretti, et al., J. Bacteriol. 169:4271–4278 (1987)) for which no catalytically involved residues have been identified. However, sequence alignment techniques (Devulapalle, et al., Protein Science 6:2489–2493 (1997); MacGregor, et al., FEBS Let. 378: 263–266 (1996)) have shown significant homologies between GTFs and alpha amylase with respect to several invariant residues important to the catalytic activity of the alpha amylase family, and have suggested that the $(\beta,\alpha)_8$ barrel element may also be a feature of the GTF catalytic domain. Strengthening this conclusion are site-directed mutagenesis studies (Devulapalle, et al., Protein Science 6:2489–2493 (1997); Tsumori, et al., Infect. Immun. 179: 3391–3396 (1997)) which showed that modification of aspartates or glutamates in GTF, which aligned with the catalytically important residues in the β4, β5, and β7 strands of alpha amylases, drastically reduced GTF catalytic activity.

Since residues in or near the putative β5 and β7 strands of GTF thus appear to be functionally important, it was of interest to determine whether significant antigenic epitopes exist within these sites of GTF catalytic activity and whether antibody to these putative epitopes could inhibit enzyme activity. Under the hypothesis that sequential epitopes within these regions could be mimicked by synthetic peptides, two synthetic peptide constructs were prepared whose sequences contained the β5 and β7 strands, as well as adjacent residues that were implicated in catalytic activity by modeling and site-directed mutagenesis techniques (MacGregor et al., *FEBS Let.* 378:263–266 (1996); Tsumori et al., *Infect. Immun.* 179:3391–3396 (1997)). These peptide constructs were then assessed for their ability to induce serum IgG and salivary IgA antibody to peptide and to *S. mutans* GTF, as well as for their ability to inhibit the catalytic activity of mutans streptococcal GTF.

The compositions of the present invention, e.g., vaccine compositions and immunogenic compositions, comprise at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. The desired effect of these compositions is interruption of the cariogenic process, resulting in reduction, i.e., lessening or prevention, of dental caries.

The primary sequences of several mutans streptococcal GTFs have been deduced from DNA studies (Ferretti et al., *Infect. Imm.* 56:1585–1588 (1988); Russell et al., *J. Dental Res.* 67:543–547 (1988); Uoda et al., *Gene* 69:1101–1109 (1988)). Although GTFs are large molecules, they function through a few discrete sites, which include the catalytic and glucan-binding sites. Primary sequences have been identified which provisionally include these sites (Mooser et al., *J. Dental Res.* 69:325 (1990); Russell et al., *J. Dental Res.* 67:543–547 (1988)).

As used herein, a vaccine composition is a composition which elicits an immune response in a mammal to which it is administered and which protects the immunized mammal against subsequent challenge by the immunizing agent or an immunologically cross-reactive agent. Protection can be complete or partial (i.e., a reduction in symptoms or infection as compared with an unvaccinated mammal). An immunologically cross-reactive agent can be, for example, the whole protein (e.g., glucosyltransferase) from which a sub-unit peptide used as the immunogen is derived. Alternatively, an immunologically cross-reactive agent can be a different protein which is recognized in whole or in part by the antibodies elicited by the immunizing agent.

As used herein, an immunogenic composition is intended to encompass a composition which elicits an immune response in a mammal to which it is administered and which may or may not protect the immunized mammal against subsequent challenge with the immunizing agent.

Peptides which are particularly useful in the present invention are peptides which consist essentially of an amino acid sequence of GTF comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof. For example, the amino acid sequence can be the amino acid sequence of the EAW peptide (ANDHLSILEAWSDNDTPYLHD; (SEQ ID NO: 1)) or the HDS peptide (VPSYSFIRAHDSEVQDLIA; (SEQ ID NO: 2)). The invention also relates to the GLB peptide (TGARTINGQLLYFRANGVQVKG; (SEQ ID NO: 3)). Appropriate amino acid sequences will contain one or more of aspartate 413, aspartate 451, aspartate 562, aspartate 567, histidine 561, tryptophan 491, glutamate 489, arginine 449, or equivalents of these amino acids. Aspartate 413, aspartate 451, aspartate 562, and aspartate 567 refer to the aspartate residues at amino acid positions 413, 451, 562 and 567, respectively, of *S. mutans* GTF-B. As used herein, equivalents of these aspartate residues are intended to include catalytic aspartate residues present at equivalent sites (positions) in other mutans streptococcal GTFs (see, for example, Table 1). That is, the amino acid position numbers of the aspartate residues can be different from 413, 451, 562, and 567 in other mutans streptococcal GTFs. These equivalent aspartate residues can be identified, for example, by aligning the amino acid sequences of other streptococcal GTFs based on homology to *S. mutans* GTF-B using methods known in the art. In addition, the characterization of the catalytic properties of an aspartate which is equivalent to aspartate 413, 451, 562, or 567 can be determined by methods described herein or methods known in the art (see, for example, Funane et al., *Biochem.* 32:13696–13702 (1993)).

Similarly, histidine 561, tryptophan 491, glutamate 489 and arginine 449 refer to the histidine, tryptophan, glutamate and arginine residues, respectively, at amino acid positions 561, 491, 489 and 449, respectively, of *S. mutans* GTF-B. As used herein, equivalents of these histidine, tryptophan, glutamate and arginine residues are intended to include histidine, tryptophan, glutamate and arginine residues, respectively, present at equivalent sites (positions) in other mutans streptococcal GTFs (see, for example, Table 1). That is, the amino acid position numbers of these residues can be different in other mutans streptococcal GTFs. These equivalent residues can be identified, for example, by aligning the amino acid sequences of other streptococcal GTFs based on homology to *S. mutans* GTF-B. In addition, the characterization of the properties of amino acid residues which are equivalent to, e.g., histidine 561 can be determined by methods described herein or methods known in the art (see, for example, Funane et al., *Biochem.* 32:13696–13702 (1993)).

Useful peptides will be of sufficient length to raise an immune response in a mammal to whom it is administered but will be less than the complete amino acid sequence of the intact GTF enzyme. Typically, the peptide will be at least 5–7 amino acids in length. Preferably the peptide will be at least 12 amino acids in length; more preferably the peptide will be at least 19, 20 or 21 amino acids in length.

The immune response which is raised can comprise a B cell response, a T cell response or both a B cell and T cell response. The B cell response is associated with the appearance of mucosal antibody, which is predominately IgA, and systemic antibody, which is predominantly IgG. The antibodies elicited by immunization will preferably recognize both the immunizing agent and an immunologically cross-reactive agent. In a preferred embodiment the antibody response will be sufficient to protect the immunized mammal against subsequent challenge or infection with the immunizing agent or an immunologically cross-reactive agent.

Although the vaccine composition of the present invention can contain one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered, preferred embodiments of the vaccine composition of the present invention contain two or more of such peptides.

Those skilled in the art will be able to determine other immunologic domains of GTF, as well as additional immunologic components of non-GTF origin which enhance adjuvanticity or produce an immunogenic response against other infectious agents, suitable for use in the vaccine composition. For example, the peptides disclosed herein can be valuably combined in a vaccine or immunogenic composition with one or more CAT, GLU, GGY, AND or SAND peptides or surface binding domain peptides such as those disclosed in U.S. Pat. No. 5,686,075 and in U.S. patent application Ser. No. 08/967,573 (Smith and Taubman), the entire teachings of which are incorporated herein by reference. In particular embodiments, the vaccine or immunogenic composition of the present invention can comprise an additional immunologic component which is an immunogenic portion of a pathogen such as, but not limited to, diphtheria, pertussis, tetanus, measles and polio virus, resulting in a multivalent vaccine producing protection against more than one infectious disease or agent. Ultimately, a multivalent vaccine can be produced which incorporates relevant protective epitopes and appropriate adjuvant sequences targeting early childhood infections.

The peptides present in the vaccine composition of the present invention may be designed in a number of ways to enhance immunogenicity. In one embodiment in which the vaccine composition contains one or more peptides, the peptide is conjugated to a known protein, (such as tetanus toxoid) or a carrier (such as a synthetic polymer carrier) to give a macromolecular structure to the vaccine which thereby enhances immunogenicity. For example, suitable peptide(s) are incorporated into a microparticle or microsphere, e.g., a PLGA (poly(lactide-co-glycolide) adjuvant) microparticle, for improved delivery and immune response. Different particles or spheres have different release profiles depending on properties, such as polymer material, pore size, total particle/sphere size, and degradation kinetics. Such bioadhesive microparticles can facilitate primary and secondary mucosal antibody formation. Microparticles prepared from the biodegradable and biocompatible polymers, the poly(lactide-co-glycolides) or (PLG), have been shown to be effective adjuvants for a number of antigens. Moreover, PLG microparticles can control the rate of release of entrapped antigens and therefore, offer potential for the development of single-dose vaccines. To prepare single-dose vaccines, microparticles with different antigen release rates are combined as a single formulation to mimic the timing of the administration of booster doses of vaccine. Adjuvants can also be entrapped within the microparticles or, alternatively, adjuvants can be co-administered.

Other examples of suitable microparticles or microspheres, which can be mixed with or loaded with the proteins, peptides, or antibodies described herein, include, but are not limited to, poly(sebacic anhydride) (PSA) microspheres (Berkland et al., J. Controlled Release vol. 24 (2003)); poly(ethylene glycol)/polylactide nano-particles (Caliceti et al., J. Controlled Release vol. 24 (2003)); oligo(poly(ethylene glycol) fumarate) (OPF) (Holland et al., J. Controlled Release vol. 24 (2003))

Other suitable biocompatible, biodegradable polymers include, for example, poly(lactides), poly(glycolides), poly (lactide-co-glycolides), poly(lactic acid)s, poly(glycolic acid)s, poly(lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalate)s, biodegradable polyurethanes, blends and copolymers thereof.

Further, the terminal functionalities of the polymer can be modified. For example, polyesters can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 6,000 to about 31,000 Daltons.

The microparticles or microspheres are 0.25–6.0 microns in dimension. Suitable microparticles are 0.25, 0.50, 0.75, 1.0, 1.5, 2.0, 2.5, 3.0, 3.5, 4.0, 4.5, 5.0, 5.5, or 6.0 microns.

A sustained release composition of the invention contains from about 0.01% (w/w) to about 50% (w/w) of protein, peptide, or antibody incorporated into particles. The amount of such particles used will vary depending upon the desired effect of the protein, peptide, or antibody, the planned release levels, the times at which protein, peptide, or antibody should be released, and the time span over which the protein, peptide, or antibody will be released. A preferred range of particle loading is between about 0.1% (w/w) to about 30% (w/w) protein, peptide, or antibody to particles. A more preferred range of protein, peptide, or antibody to particle loading is between about 0.1% (w/w) to about 20% (w/w) particles. The most preferred loading of the particles is about 15% (w/w).

The sustained release composition of this invention can be formed into many shapes such as a film, a pellet, a cylinder, a disc or a microparticle A microparticle, as defined herein, comprises a polymeric component having a diameter of less than about one millimeter and having protein-, peptide-, or antibody-loaded particles dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 2% (w/v) to about 20% (w/v) polymer. A polymer solution containing 5% to about 10% (w/w) polymer is most preferred.

The method for forming a composition for modulating the release of a biologically active agent from a biodegradable polymer is further described in U.S. Pat. No. 5,656,297 to Bernstein et al. One suitable method for forming a sustained release composition from a polymer solution is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al. Another method for forming sustained release microparticles from a polymer solution is described in U.S. Pat. No. 5,019,400, issued to Gombotz et al. This method of microsphere formation, as compared to other methods, such as phase separation, additionally reduces the amount of protein, peptide, or antibody required to produce a sustained release composition with a specific protein, peptide, or antibody content.

The proteins, peptides, or antibodies described herein can also be conjugated to polymers, such as N-(2-hydroxypropyl)methacrylamide (HPMA) copolymer (Nan et al., *J. Controlled Release* vol. 24 (2003); polyvinylpyrrolidone (PVP) (Souza et al., *J. Controlled Release* vol. 24 (2003)); branched poly(L-glutamic acid) attached to poly(amidoamine) (PAMAM) dendrimer or polyethyleneimine (PEI) cores (Tansey et al., *J. Controlled Release vol.* 24 (2003)); or bacterial polysaccharide or lipopolysaccharide (LPS) (see e.g., Frosch, M. in "Vaccine Delivery Strategies").

Additionally, other ways of enhancing immune responses to mucosally applied peptides (antigens) include use of mucosal adjuvants such as detoxified versions of tetanus toxin (e.g. tetanus toxin Fragment C), cholera toxin or *E. coli* heat-labile toxins (Smith et al., *Infect. Immunity* 69(8): 4767–4773 (2002)). Other immunostimulatory adjuvants include LPS derivatives, saponins, CpG oligonucleotides, and cytokines.

In a preferred embodiment in which the vaccine composition contains at least two peptides, the peptides are synthesized and covalently attached to a peptidyl core matrix to yield a macromolecule with a high density of peptides in a single structure. Each peptide in such a structure consists essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. The peptidyl core matrix can consist of amino acids such as lysine, arginine and histidine. In particular, at least 2 peptides are synthesized on a core matrix of at least one lysine to yield a macromolecular vaccine composition. Particularly, at least 2 peptides are synthesized on a core matrix of 3 lysines. In a preferred embodiment, a vaccine composition is designed in which four peptides of the present invention are synthesized and covalently attached to a core matrix of 3 lysines yielding a radially branched peptide with four dendritic arms. In this embodiment, the four peptides present can be the same or different. Those skilled in the art will be able to determine other variations of synthesizing and covalently attaching vaccine compositions of the present invention to a peptidyl core matrix by employing routine experimentation.

The present invention also pertains to pharmaceutical compositions comprising at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. For instance, the peptide of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous peptides at the site of treatment include, but are not limited to, intradermal, intramuscular, intraperitoneal, intravenous, subcutaneous, oral, sublingual, intraocular and intranasal. Other suitable methods of introduction can also include rechargeable or biodegradable devices and slow release polymeric devices. The pharmaceutical compositions of this invention can also be administered as part of a combinatorial therapy with other agents.

The present invention also relates to antibodies which bind a polypeptide of the present invention. For instance, polyclonal and monoclonal antibodies, including nonhuman and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); WO 97/08320 (Morphosys) and U.S. Pat. No. 5,225,539 (Winters)) which bind to the described polypeptides are within the scope of the invention. A mammal, such as a mouse, rat, hamster or rabbit, can be immunized with an immunogenic form of the polypeptide (e.g., a peptide comprising an antigenic fragment which is capable of eliciting an antibody response). Techniques for conferring enhanced immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and F(ab)$_2$. Antibodies described herein can be used to inhibit the activity of GTF, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the polypeptide or GTF protein.

The present invention further relates to a method of provoking an immune response to glucosyltransferase in a mammal by administering a peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. Preferably, the immune response results in interference with the enzymatic activity of glucosyltransferase in mammals after administration of the vaccine composition. The immune response elicited by the compositions and methods of the invention can be humoral or systemic; for example, the immune response can be a mucosal response. The immune response elicited by the method of the present invention results in reduction of the colonization or accumulation of mutans streptococcal strains in the mammal to whom the vaccine or immunogenic composition is administered.

The invention also relates to a method of immunizing a mammal against dental caries comprising administering a peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in the mammal, to the mammal.

The compositions of the present invention can be administered to any mammal in which the prevention and/or reduction of dental caries is desired. Suitable mammals include primates, humans, cats, dogs, mice, rats and other mammals in whom it is desirable to inhibit dental caries. The present invention provides a vaccine that is useful for preventing, halting or reducing the progression of dental caries in a mammal to whom the vaccine is administered.

In the method of the present invention of provoking an immune response to glucosyltransferase, mammals in which an immune response to glucosyltransferase is desired are given the vaccine or immunogenic compositions described herein. The vaccine composition can be included in a formulation which is administered to an individual being treated; such a formulation can also include a physiologically compatible carrier (e.g., a physiological buffer), stabilizers, flavorants, adjuvants and other components. The vaccine can be administered by a variety of routes (e.g., parenterally, intranasally, intraocularly, intravenously, orally) and the components of the formulation will be selected accordingly. The amount to be administered and the frequency of administration can be determined empirically and will take into consideration the age and size of the mammal being treated and the stage of the dental caries disease (e.g., prior to colonization of Mutans streptococci, soon after colonization of Mutans streptococci or in later stages of colonization).

Studies (Taubman et al., *J. Dent. Res.* 76:347 (1997)) indicate that multiepitopic peptide constructs induce enhanced immune responses. This strategy also could be used to increase the immune potential of the EAW/HDS/GLB peptide sequences described herein. Moreover, the combination of sequences from several strains into a synthetic or recombinant multi-epitopic construct could increase the protective potential of subunit vaccines for dental caries.

Figure 1:
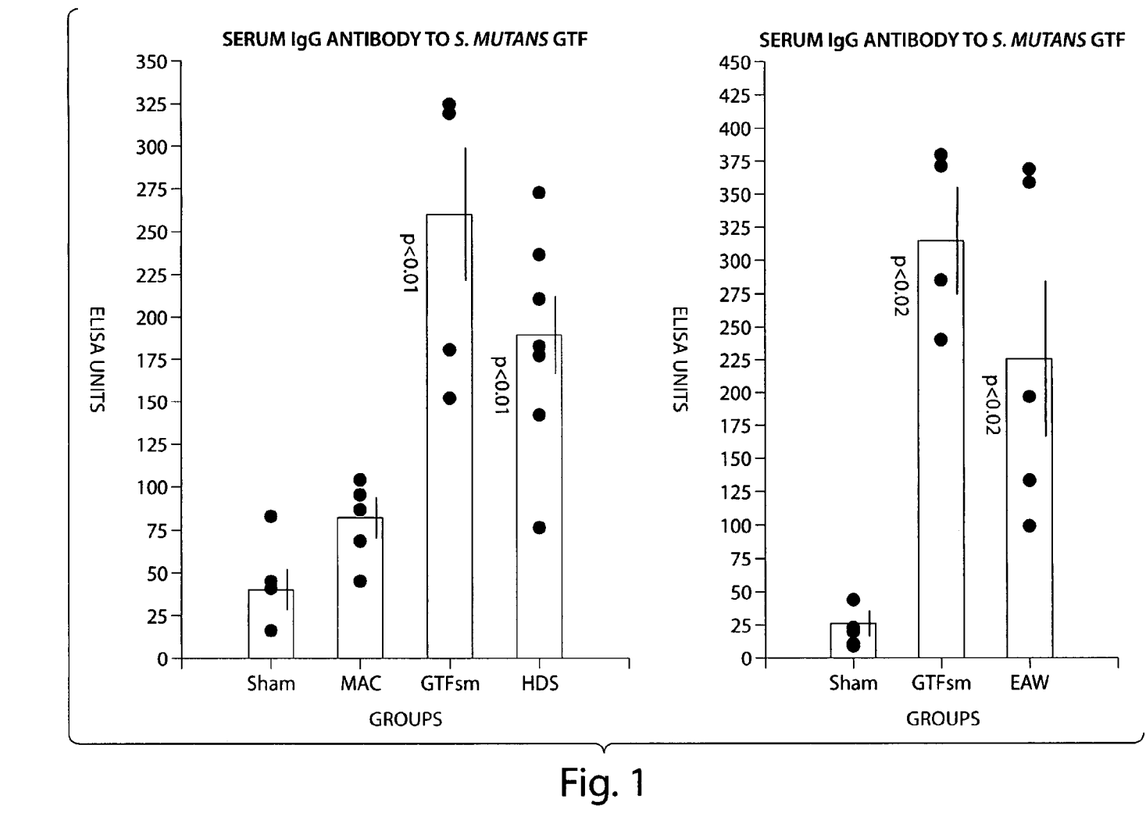
FIG. 1 is a graph showing the results when IgG antibody reactivities to S mutans GTF were evaluated in ELISA in rat sera taken 42 days after initial injection (2 injections). The left and right panels represent different experiments utilizing identical immunization protocols. Bars indicate the mean absorbance for all rat sera of the indicated group (n=4–7), tested at 1:400 dilutions, at least in duplicate. Vertical bars indicate two standard errors. The levels of significance, compared with the sham group, using the Kruskal-Wallace ANOVA on ranks, are indicated alongside the bars.
Figure 2:
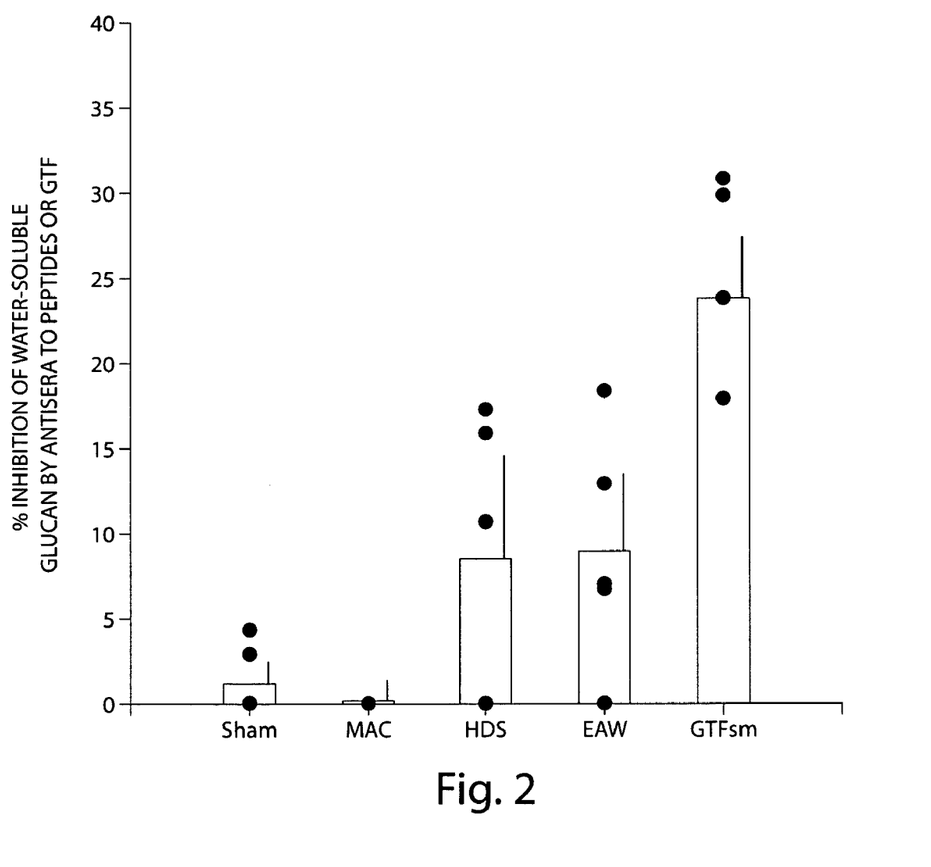
FIG. 2 is a graph showing the percent inhibition of the S. mutans GTF-mediated incorporation of $^{14}C$ glucose from labeled sucrose into water-soluble glucan by sera from peptide or GTF-injected rats. Bars indicate the mean inhibition for rat sera (n=4–6) of the indicated peptide-injected groups, tested at 1:10 dilutions, or the S. mutans GTF-injected group, tested at 1:50 dilutions. The vertical bar indicates one standard deviation. Closed circles indicate the inhibition levels of individual rat sera. Data are expressed as the percent $^{14}C$ glucose incorporation of individual sera, compared with the mean $^{14}C$ glucose incorporation by four sera from sham-injected rats tested under the same protocol (mean incorporation=830 cpm).

Many lines of evidence suggest that mutans glucosyltransferases require the interaction of several sequentially separated amino acid residues for their catalytic activity. Sequence alignments of GTFs with alpha-amylases have suggested that a similar $(\beta,\alpha)_8$ barrel structure is present in the catalytic domain of both protein families (Devulapalle, et al., *Protein Science* 6:2489–2493 (1997), MacGregor, et al., *FEBS Let.* 378:263–266 (1996)). Supporting this suggested structure is the observation that GTF activity can be significantly inhibited by site-directed mutagenesis of residues that correspond to invariant amino acids which are catalytically important in the $(\beta,\alpha)_8$ barrel domain of alpha amylases (Devulapalle, et al., *Protein Science* 6:2489–2493 (1997); Tsumori, H et al., *Infect. Immun.* 179:3391–3396 (1997)). The immunological findings of the present study also support the catalytic importance of residues in equivalent GTF regions. In these studies, HDS and EAW (Table 1), two peptide constructs whose sequences are adjacent to the β5 and β7 strand elements of mutans streptococcal GTFs, induced high levels of serum IgG and salivary IgA antibody, not only to themselves (Tables 2 and 3), but also to *S. mutans* GTF (FIG. 1). Furthermore, these peptides also had the ability to induce antibody which could inhibit the water-soluble glucan synthetic activity of *S. mutans* GTF (FIG. 2).

Alpha amylases contain three catalytic sites which are located in or adjacent to the β4, β5 and β7 strands. Several catalytically involved amino acid residues have been implicated within analogous regions of GTF. One of these, an aspartate (Asp 451 in *S. mutans* GTF-B) corresponding to an invariant catalytic aspartate in the alpha amylase family (Asp 206 of taka-amylase A), has been shown by Mooser and coworkers (Mooser, et al., *J. Biol. Chem.* 266:8916–8922 (1991)) to be involved in glucosyl-intermediate formation by GTF. It has been reported that the synthetic peptide construct, CAT, whose sequence contains the β4 strand and includes residues corresponding to the invariant Arg-449 and the above-mentioned Asp-451, can induce antibody that binds to intact GTF, significantly inhibits GTF activity, and can induce protective immunity for experimental dental caries (Smith, et al., *Infect. Immunity* 62:5470–5476 (1994), Taubman, et al., *Infect. Immun.* 63:3088–3093 (1995)). Recently, Devulapulle and Mooser (Devulapalle, et al., *Protein Science* 6:2489–2493 (1997)) mutated the comparable aspartate in *Streptococcus downei* GTF which resulted in an almost complete loss of catalytic activity.

Within the β5-associated strand of alpha amylases is a glutamate residue (position 230 in taka-amylase A) which is considered to serve catalytically as a proton donor (Matsuura, et al., *J. Biochem.* 95:697–702 (1984)). Site-directed mutagenesis of the analogous residue in *S. downei* GTF (Glu-489 in *S. mutans* GTF-B) to glutamine resulted in a catalytically inactive enzyme (Devulapalle, et al., *Protein*

Science 6:2489–2493 (1997)). Mutagenesis of Trp-491 in *S. mutans* GTF-B, highly conserved in all mutans streptococcal GTFs (Table 1), also eliminated detectable enzyme activity (Tsumori, et al., *Infect. Immun.* 179:3391–3396 (1997)). The EAW peptide sequence overlapped both of these important residues as well as the complete β5 strand sequence. Antibody induced by the EAW peptide construct could bind to and inhibit *S. mutans* GTF.

The HDS peptide construct contains several residues which have been implicated in GTF function. His-561 and Asp-562 in *S. mutans* GTF-B are invariant in mutans streptococcal GTFs. The analogous histidine in alpha amylases helps to stabilize transition states (Sogaard, et al., *J. Biol. Chem.* 268:22480–22484 (1993)), while the aspartate stabilizes the reaction intermediate carbonium cation (Matsuura, et al., *J. Biochem.* 95:697–702 (1984)). Site directed mutagenesis of the equivalent histidine and aspartic acid residues in mutans streptococcal GTFs catalytically inactivated the enzyme (Devulapalle, et al., *Protein Science* 6:2489–2493 (1997); Tsumori, et al., *Infect. Immun.* 179: 3391–3396 (1997)). Also contained within the HDS peptide sequence is an aspartate, equivalent to Asp-567 in GTF-B, which has been shown to influence the solubility of the glucan synthesized by GTF (Shimamura, et al., *J. Bact.* 176:4845–4850 (1994)). Aspartic acid is invariant at this position in all mutans streptococcal GTFs, although it is not conserved in alpha amylases, presumably because its function is irrelevant to amylolytic activity. Thus, antibody directed to the HDS peptide construct could be expected to influence several aspects of GTF activity. In the present study, most rats responded to HDS-peptide construct immunization with levels of antibody to GTF that were within the range of sera from rats injected with intact *S. mutans* GTF. Many of these sera also inhibited the water-soluble glucan synthetic activity of *S. mutans* GTF which is consistent with the presence of putative functional residues within this sequence.

Peptide-injected rat sera did not detectably inhibit water-insoluble glucan synthesis under the conditions of the assay. This lack of water-insoluble glucan inhibition may be related to the expected lower affinity and avidity of the anti-peptide antibody or be a consequence of assay conditions, such as the mixture of *S. mutans* GTF isotypes used for synthesis or the lack of primer dextran. Interestingly, antisera to intact *S. mutans* GTF also were less effective as inhibitors of water-insoluble, compared with water-soluble, glucan synthesis.

The MAC peptide construct was selected for control purposes, because its sequence (amino acids 342–356) lay outside the GTF $(\beta,\alpha)_8$ barrel domain predicted by MacGregor and coworkers (MacGregor et al., *FEBS Let.* 378: 263–266 (1996)) or within a non-catalytically implicated approximately 200 residue loop within the $(\beta,\alpha)_8$ barrel domain of GTF predicted by Devulapalle and Mooser (Devulapalle et al., *Protein Science* 6:2489–2493 (1997)). Also this sequence bore no homology with sequences associated with catalytic function by biochemical (Funane et al., *Biochem.* 32:13696–13702 (1993); Mooser et al., *J. Biol. Chem.* 266:8916–8922 (1991)) or molecular genetic techniques (Chia et al., *Immun.* 61:4689–4695 (1993); Devulapalle et al., *Protein Science* 6:2489–2493 (1997); Tsumori et al., *Infect. Immun.* 179:3391–3396 (1997)). Neither serum IgG nor salivary IgA antibody to the HDS peptide construct showed any reactivity with the MAC peptide (Table 2). The MAC peptide construct was less immunogenic and induced less GTF-inhibitory antibody than did the HDS or EAW constructs, further supporting the catalytic significance of the residues within the latter two peptide sequences. Interestingly, a peptide sequence corresponding to MAC was immunogenic when fed (Dertzbaugh et al., *Infect. Immun.* 58:70–79 (1990)) or injected (Dertzbaugh and Macrina, *Immun.* 58:1509–1513 (1990)) as a protein chimera, fused to the sequence of the B subunit of cholera toxin (CTB). This difference in reactivity between the chimeric protein (Dertzbaugh and Macma, *Immun.* 58:1509–1513 (1990)) and that of the MAC peptide construct could be because the former had highest homology with *S. mutans* GTF-B and GTF-C, while the MAC peptide in the present study was identical to the respective sequences in *S. sobrinus* and *S. downei* GTF-I (Table 1). In addition, the fusion with CTB undoubtedly influenced the immunogenicity of the protein chimera.

Thus, these data indicate that sequences containing functionally important residues associated with the β5 and β7 barrel elements are immunogenic and can induce systemic and mucosal antibody responses that can lead to loss of enzyme function. It has been shown that antibody levels induced by other catalytically associated peptides can be increased by combination with functionally associated GTF peptides that also contain a strong T cell epitope (Taubman et al., abstr. 2666, p. 347, *In J. Dent. Res.* 76 (1997)). Combination of HDS and or EAW with such peptides may also enhance immune responses to these important epitopes. Since both EAW and HDS peptide constructs also gave rise to significant levels of salivary IgA antibody in many animals, di- or multi-epitopic constructs could be expected to also increase mucosal immunity, thus potentiating their application as subunit vaccines for dental caries.

The invention will now be further illustrated by the following non-limiting examples. The teachings of all references cited herein are incorporated herein by reference in their entirety.

EXAMPLES

Example 1

Materials and Methods

Peptide Constructs:

Three peptides were synthesized. Two of the sequences selected for synthesis (EAW and HDS) were based on putative catalytic regions within the predicted $(\beta,\alpha)_8$ barrel structure of GTF (Devulapalle et al., *Protein Science* 6:2489–2493 (1997); MacGregor et al., *FEBS Let.* 378: 263–266 (1996)). EAW is a 21-mer peptide construct whose sequence contains the β5 strand sequence, as well as catalytically implicated Glu-489 and Trp-491 (Table 1). HDS is a 19-mer peptide whose sequence contains the β7 strand sequence, as well as catalytically implicated His-561 and Asp-562 (Table 1). Both EAW and HDS sequences are highly conserved among all mutans streptococcal GTFs, and were identical to the respective *S. mutans* GTF-B sequence (Table 1). A third peptide (MAC) was synthesized to serve as a control for sequence outside the $(\beta,\alpha)_8$ barrel domain predicted by MacGregor and coworkers (MacGregor et al., *FEBS Let.* 378:263–266 (1996)) and had 100% homology with the respective sequence of GTF-I of *S. sobrinus* and *S. downei*. Peptides were synthesized (Applied Diagnostics, Foster City, Calif.) using the stepwise solid phase method of Merrifield (Merrifield, *J. Amer. Chem. Soc.* 85:2149–2154 (1963)) on a core matrix of lysines to yield macromolecules with four identical peptides per molecule, after the method of Tam (Tam, *Proc. Natl. Acad. Sci. USA* 85:5409–5413 (1988)). Purity (>90%) was assessed using HPLC, amino acid analysis, and molecular weight determination by mass spectrometry.

Glucosyltransferases:

GTFs from *S. mutans* SJ and *S. sobrinus* 6715 were obtained as previously described (Smith, et al., *Infect. Immunity* 62:5470–5476 (1994); Taubman, et al., *J. Oral Pathol.* 17:466–470(1988)). After bacterial growth in glucose-containing defined medium, enzymes were isolated from culture medium by affinity chromatography on Sephadex G-100 (Pharmacia Fine Chemicals, Piscataway, N.J.) with 3M guanidine HCl as the eluting solvent. These GTF-rich pools were then subjected to FPLC liquid chromatography on Superose 6 (Pharmacia) with 6 M guanidine HCl for elution. The gel filtration step removes non-GTF and other glucan-binding proteins from GTF preparations, as evidenced by the fact that the protein bands observed after SDS-polyacrylamide gel electrophoresis were all associated with enzymatic activity after incubation of duplicate gels in sucrose. This *S. mutans* GTF preparation (GTFsm) synthesized both water insoluble and water soluble glucan in both tube and filter assays (Taubman, et al., *J. Oral Pathol.* 17:466–470 (1988)) and was used for injection, inhibition assays and ELISA measurements of antibody activity.

Immunogenicity of Peptides:

Sprague Dawley CD strain 42 day-old male rats (Charles River Laboratories, Wilmington, Mass.) were used for injection. Two experiments were performed. In the first experiment groups of 4–7 rats were injected subcutaneously in the vicinity of the salivary glands with 50 µg each of either HDS or MAC peptide constructs, or 10 µg of *S. mutans* GTF, or sham-immunized with buffer alone. In the second experiment groups of 4–6 rats were injected with 50 µg of the EAW peptide construct, 10 µg of *S. mutans* GTF, or sham-immunized. The remainder of the experimental protocol was identical. The initial injection included complete Freund adjuvant (CFA; Difco Laboratories, Detroit, Mich.). Twenty one days later animals were again immunized with antigen in incomplete Freund's adjuvant (FA). Animals were bled and salivated prior to injection, at day 21 and day 42 after the first injection. Sera and clarified salivas were stored at −70° C. prior to assay.

ELISA:

Serum IgG and salivary IgA antibodies were tested by enzyme-linked immunosorbent assay (ELISA). Polystyrene microtiter plates (Flow Laboratories) were coated with 2.5 µg/ml of each peptide construct or 0.5 µg/ml of *S. sobrinus* or *S. mutans* GTF. Antibody activity was then measured by incubation with 1:400 and 1:4000 dilutions of sera, or 1:4 and 1:8 dilutions of saliva. Plates were then developed for IgG antibody with rabbit anti-rat IgG, followed in sequence by alkaline phosphatase goat anti-rabbit IgG (Biosource Inc.) and p-nitrophenylphosphate (Sigma Chemical Co., St. Louis, Mo.). A mouse monoclonal reagent to rat α chain (Zymed, South San Francisco, Calif.) was used with biotinylated goat anti-mouse IgG (Zymed) and avidin-alkaline phosphatase (Cappel) to reveal levels of salivary IgA antibody to peptides. Reactivity was recorded as absorbance ($A_{405\ nm}$) in a micro plate reader (Biotek Instruments, Winooski, Vt.). Data are reported as ELISA units (EU) which were calculated relative to the levels of appropriate reference sera or salivas from Sprague Dawley rats twice immunized with the respective peptide construct. Dilutions of sera producing an $A_{405\ nm}$ of approximately 1.0 were considered 100 EU for serum IgG antibody measurements. These corresponded to dilutions of 1:51,200, 1:25,000, 1:12,800 or 1:6,400 for serum antibody to *S. sobrinus* GTF, *S. mutans* GTF, EAW or HDS constructs, respectively. Dilutions of saliva producing an $A_{405\ nm}$ of approximately 0.8 were considered 100 EU for salivary IgA antibody measurements. These correspond to dilutions of 1:4 for salivary IgA to both EAW and HDS constructs.

Antibody Inhibition of Glucan Synthesis:

Selected rat sera were evaluated for their ability to inhibit water-soluble glucan synthesis catalyzed by *S. mutans* GTF, using a filter assay. This GTF preparation contains a mixture of GTFs, including GTF-B which has complete homology with both peptide constructs in the respective region (Table 1). Ten µl volumes of diluted sera (1:10 dilutions in 0.02M sodium phosphate buffered saline and 0.2% sodium azide [PBSA], pH 6.5) were preincubated with the GTF for 1 hour at 37° C. in a total volume of 0.04 ml PBSA. The 1.7 mg sucrose and 24 nCi of [$^{14}$C-glucose]-sucrose (approximately 35,000 cpm) were added in 0.2 ml PBA in the absence of primer (Taubman, et al., *Infect. Immun.* 63:3088–3093 (1995)). Incubation proceeded overnight at 37° C. after which water-insoluble glucan was collected on, and water-soluble glucan collected after passage through Whatman GF/F glass fiber filters. Water-insoluble glucan collected on filters was washed and retained radioactivity determined as previously reported (Taubman, et al., *J. Oral Pathol.* 17:466–470 (1988)). Water soluble glucan was precipitated with 70% ethanol and radioactivity determined as previously described (Taubman, et al., *J. Oral Pathol.* 17:466–470 (1988)). Under the conditions of this assay, approximately 800 counts per minute (cpm) were incorporated into water-soluble glucan, and 3000 cpm were incorporated into water-insoluble glucan, in the presence of sham immune sera. Percentage inhibition of enzyme activity was calculated using these mean sham incorporation cpm values as the 100% incorporation levels.

Results

Immunogenicity of Peptides:

Antibody levels measured in sera collected 42 days after initial antigen injection are presented in Tables 2 and 3. Results are shown for sera tested at 1:400 dilutions. Serum antibody could be detected 21 days after the initial injection in most HDS and EAW-injected rats. By day 42, all HDS- (Table 2) and EAW-(Table 3) peptide injected rats had high levels of serum IgG antibody to epitope(s) associated with the respective peptide. In fact, serum antibody could be detected at dilutions greater than $10^5$ in some sera from rats injected with HDS and EAW peptide constructs. In contrast, injection with MAC induced IgG antibody that could be detected at 1:400 diluted sera in 4/5 rats, but was absent in 3 of 5 rat sera at a dilution of 1:1600. No significant reactivity with HDS or EAW was observed with sera from sham, MAC or GTF-injected groups. Also, sera from HDS or EAW-injected rats did not cross react with the heterologous peptide (Tables 2 and 3).

Two immunizations with the HDS and EAW peptide constructs also induced significant levels of salivary IgA antibody that were reactive with the respective peptide in all rats by day 42 (Tables 2 and 3). The HDS peptide construct also induced elevated salivary IgA immune responses in 3/7 HDS-injected rats on day 21 after one immunization, although no antibody to EAW could be detected at this time in EAW-injected rats. Thus, both the EAW and HDS peptide constructs have significant systemic and mucosal immunogenicity when given by the subcutaneous route of injection.

Reactivity with GTF:

All antisera were evaluated by ELISA for IgG antibody reactive with S. mutans GTF preparations. Sera from all rats injected with S. mutans GTF and EAW had elevated levels of IgG antibody to S. mutans GTF at day 21 and day 42 (FIG. 1). Anti-GTF antibody levels in day 42 sera of 2/5 EAW-injected rats were within the range of those of the GTF-injected rats, suggesting that the epitope(s) presented on the EAW-peptide construct is(are) prominent on native GTF. Sera from 6/7 rats injected with the HDS peptide construct demonstrated IgG antibody that reacted with S. mutans GTF on day 42 (FIG. 1). At that time, 5/7 HDS-injected rats showed serum IgG reactivity to GTF within the range of the GTF-injected rats. In contrast, antibody to MAC-injected rats had significantly lower levels of antibody reactive with S. mutans GTF.

Inhibition of GTF Activity:

Sera from sham-, GTFsm-, and peptide construct-injected rats were evaluated for their ability to inhibit the formation of water-soluble and water-insoluble glucan by S. mutans GTF. Sera from many, but not all, EAW, and HDS-injected rats inhibited the ability of S. mutans GTF to synthesize water-soluble glucan (FIG. 2). The level of inhibition of water-soluble glucan formation approached 20% in sera of three rats injected with EAW or HDS peptide constructs. In contrast, no serum from rats injected with the MAC peptide construct inhibited S. mutans GTF water-soluble glucan synthetic activity. Water-insoluble glucan formation by S. mutans GTF was not found to be inhibited by sera from any peptide-injected rat under the conditions of this assay.

TABLE 1

Amino acid sequence homology of MAC, EAW and HDS peptides with S. mutans, S. sobrinus and S. downei GTFs and association with β5 and β7 strand domains

| GTF/peptide (reference) | | Sequence | Homology with Peptide |
|---|---|---|---|
| MAC peptide | | PQWNGESEKPYDDHL (SEQ ID NO: 4) | |
| GTF-B | S. mutans[1] | 342 - SAWNSDSERPFDDHL (SEQ ID NO: 5) | 53% |
| GTF-C | S. mutans[2] | 368 - SAWNSDSEKPFDDHL (SEQ ID NO: 6) | 67% |
| GTF-D | S. mutans[3] | 354 - PNWNSQTESDTSAGE (SEQ ID NO: 7) | 27% |
| GTF-I | S. downei[1] | 342 - PQWNGESEKPYDDHL (SEQ ID NO: 8) | 100% |
| GTF-S | S. downei[4] | — | 0% |
| GTF2 | S. sobrinus[5] | 336 - PQWNGESEKPYDDHL (SEQ ID NO: 9) | 100% |
| † # | | | |
| EAW peptide | | ANDHLSILEAWSDNDTPYLHD (SEQ ID NO: 1) | |
| GTF-B | S. mutans | 480-ANDHLSILEAWSDNDTPYLHD (SEQ ID NO: 1) | 100% |
| GTF-C | S. mutans | 506-ANDHLSILEAWSYNDTPYLHD (SEQ ID NO: 10) | 95% |
| GTF-D | S. mutans | 494-AINHLSILEAWSDNDPQYNKD (SEQ ID NO: 11) | 68% |
| GTF-I | S. downei | 482-ANNHVSIVEAWSDNDTPYLHD (SEQ ID NO: 12) | 90% |
| GTF-S | S. downei | 467-AIDHLSILEAWSGNDNDYVKQ (SEQ ID NO: 13) | 63% |
| GTF2 | S. sobrinus | 476-ANNHVSIVEAWSDNDTPYLHD (SEQ ID NO: 14) | 84% |
| ..β5.. | | | |
| ‡↑ ◻ | | | |
| HDS peptide | | VPSYSFIRAHDSEVQDLIA (SEQ ID NO: 2) | |
| GTF-B | S. mutans | 549-VPSYSFIRAHDSEVQDLIA (SEQ ID NO: 2) | 100% |

TABLE 1-continued

Amino acid sequence homology of MAC, EAW and HDS peptides with
S. mutans, S. sobrinus and S. downei GTFs and association with
β5 and β7 strand domains

| GTF/peptide | (reference) | Sequence | Homology with Peptide |
|---|---|---|---|
| GTF-C | S. mutans | 575-VPSYSFIRAHDSEVQDLIRNII (SEQ ID NO: 15) | 95% |
| GTF-D | S. mutans | 571-MANYIFIRAHDSEVQTVIAKII (SEQ ID NO: 16) | 63% |
| GTF-I | S. downei | 551-VPSYSFARAHDSEVQDLIRDII (SEQ ID NO: 17) | 84% |
| GTF-S | S. downei | 534-VPNYVFIRAHDSEVQTRIAKII (SEQ ID NO: 18) | 74% |
| GTF-2 | S. sobrinus | 545-VPSYSFARAHDSEVQDIIRDII (SEQ ID NO: 19) | 84% |

†Glutamic and aspartic acids at these positions are catalytic in alpha amylases (Matsuura, et al., J. Biochem. 95:697–702 (1984); Tsumori, et al., Infect. Immun. 179:3391–3396 (1997)); modification of these amino acids in GTF leads to loss of activity (Devulapalle, et al., Protein Science 6:2489–2493 (1997); Tsumori, et al., Infect. Immun. 179:3391–3396 (1997)).
‡Histidine stabilizes transition states at this position in alpha amylases (Matsuura, et al., J. Biochem. 95:697–702 (1984); Sogaard, et al., J. Biol. Chem. 268:22480–22484 (1993)); modification of this histidine in GTF leads to loss of activity (Tsumori, et al., Infect. Immun. 179:3391–3396 (1997)).
Tryptophane is highly conserved at this position in GTF; activity is lost when mutated (Tsumori, et al., Infect. Immun. 179:3391–3396 (1997)).
¤Glucan product type changed when aspartic acid at this position in GTF is mutated (Shimamura, et al., J. Bact., 176:4845–4850 (1994)).
[1]Ferretti, et al., J. Bacteriol. 169:4271–4278 (1987)
[2]Shiroza, et al., J. Bacteriol. 169:4263–4270 (1987)
[3]Honda, et al., J Gen. Microbiol. 136:2099–2105
[4]Gilmore, et al., Infect. Immun. 58:2452–2458 (1990)
[5]Abo, et al., J. Bacteriol. 173:989–996 (1991)

TABLE 2

Serum and salivary immune responses to HDS after subcutaneous injection with MAC, EAW, or HDS peptide constructs or S. mutans GTF (n = 4–7 rats/group).

| | Mean Serum IgG EU ± SE | | | Mean Salivary IgA EU ± SE | | |
|---|---|---|---|---|---|---|
| Group | pre | day 42 | range | pre | day 42 | range |
| Sham | 0 ± 0 | 0 ± 0 | 0 | 1 ± 1 | 0 ± 0 | 0 |
| MAC | 0 ± 0 | 0 ± 0 | 0 | 0 ± 0 | 1 ± 1 | 0 |
| EAW | ND* | 0 ± 0 | 0 | ND | ND | |
| HDS | 0 ± 0 | 118 ± 18 | 99-155 | 1 ± 1 | 142 ± 36 | 16–206 |
| GTFsm | 0 ± 0 | 0 ± 0 | 0 | 0 ± 0 | 1 ± 1 | 0 |

*ND = not done

TABLE 3

Serum and salivary immune responses to EAW after subcutaneous injection with MAC, EAW, or HDS peptide constructs or S. mutans GTF (n = 4–7 rats/group).

| Injected | Mean Serum IgG EU ± SE | | | Mean Salivary IgA EU ± SE | | |
|---|---|---|---|---|---|---|
| Group | pre | day 42 | range | pre | day 42 | range |
| Sham | 0 ± 0 | 0 ± 0 | 0 | 0 ± 0 | 0 ± 0 | 0 |
| MAC | ND* | 0 ± 0 | 0 | ND | ND | — |
| EAW | 0 ± 0 | 117 ± 40 | 105–126 | 1 ± 1 | 53 ± 19 | 14–78 |
| HDS | ND | 0± | 0 | ND | ND | — |
| GTFsm | 0 ± 0 | 2 ± 2 | 0 | 0 ± 0 | 1 ± 1 | 0 |

Example 2

Preparation and Immunogenicity of Monoepitopic and Polyepitopic Tetanus Toxoid (TT)-Glucosyltransferase (GTF) Peptide Conjugate Vaccines MAP format peptide multicomponent vaccines, incorporate epitopes from separate regions of the GTF molecule and result in enhanced protective immunity. Three TT-peptide constructs were prepared to evaluate responses to monoepitopic peptides. Each peptide was synthesized with a 4 amino acid amino terminus spacer (CAGA) coupled to iodoacetylated TT. Each conjugate (TT-GLU; TT-CAT; TT-HDS) contins approximately 10 peptide moieties/TT molecule. A triepitopic TT composite (TT-GLU-CAT-HDS) was also synthesized. Five groups of Rowett rats were used to assess the immunology of these conjugates. The first group was sham immunized (salivary gland vicinity) with buffer/CFA on Day 0 and in IFA 1 week later. Other groups were immunized identically with the respective conjugates. Rats were bled 21, 28, and 35 days after IFA injection, and cervical node lymphocytes harvested for proliferation assays. Each serum (1/100) was tested vs. GLU, CAT, HDS at the same concentration in ELISA and against GTF and TT for serum IgG.

Maximum responses were seen on Day 35. All groups were statistically compared. TT-GLU and TT-GLU-CAT-HDS tested positive to GLU with mean OD405 nm of 1.099 and 1.310, respectively. Antibody to CAT was present after TT-CAT injection. Antibody to HDS was observed after each construct injection. Antibody to GTF was found after TT-HDS and TT-CAT immunization (OD of 1.321 and 0.980, respectively). Proliferative responses were observed after immunization with TT-GLU or TT-CAT.

Example 3

Functional and Immune Properties of the DGQ Peptide

The peptide DGQVQYFDEMGYQAKGKFV (SEQ ID NO: 20) (DGQ; residues 1176–1194) has been shown to reduce sucrase activity by 26% and GTF-I activity by 77%. Here, DGQ was synthesized as a four-chain MAP construct. Inhibition of GTF activity was measured by incubating peptide with GTF, $^{14}C$ glucose-labelled sucrose and dextran primer for 2 hours, followed by collection of ethanol-insoluble glucan. The effect of DGQ was compared with that of peptides shown to be associated with catalytic residues or with glucan binding activity. In separate experiments, weanling Sprague-Dawlley rats were subcutaneously immunized with DGQ or sham injected (13/group). Three weeks after the first injection, rats were bled, salivated, then infected with cariogenic *S. mutans*. Antibody levels to DGQ were measured by ELISA. Dental caries were recorded after a 76 day infection.

DGQ showed no effect on GTF activity. However, DGQ did induce serum IgG immune responses in all immunized rats (p<0.01). Some rats also had measurable salivary IgA antibody responses to DGQ. Total caries scores in DGQ-injected rats (28.6±2.4) were lower than those of sham-injected rats (44.7±7.1). Therefore, although the MAP DGQ construct did not inhibit GTF activity, it did induce a significant immune response, which unexpectedly inhibited caries development in rats.

Example 4

Expression and Delivery of GTF Peptides in *Salmonella enterica*

*Salmonella enterica* subspecies I includes *S. typhii* human adapted serotype that causes typhoid fever. This *S. typhii* does not cause disease in rats and can only be transiently recovered. Attenuation of these bacteria renders them auxotrophic for para-aminobenzoic acid and dihydroxybenzoate and they exhibit a delection of the htrA locus encoding a heat shock protein (Δaro C, Δaro D, Δhtr A CVD908-htrA). These attenuated *Salmonella* have been successfully used in humans for induction of immunity.

The GLB peptide (22 amino acids, 77% identical to GLU peptide) and GLU peptide (21 amino acids) from the glucan binding carboxy terminus of GTF were each expressed in *Salmonella tphii* strain (Δaro C, Δaro D, Δhtr A CVD908-htrA). Constructs containing 1, 2, 3, or 4 GLB copies were prepared. However, no antibody to a GLB construct or to GTF could be detected after intranasal (IN) infection or injection of rats or mice with the GLB vaccine strain. GLU has also been expressed in *S. typhii* CVD908 htrA. This organism was also instilled IN into Rowett rats (N=6) or injected into these rats (N=5). The vaccine strain also contained fragment C (FC) of tetanus toxin (TT), so that the *S. typhii* expressed a fusion protein, FC-GLU. The rats were infected for 2 consecutive days with >$10^{11}$ GLU vaccine strain or parent control (no GLU). Sera isolated 21 days after infection (or injection) were examined by ELISA for IgG antibody to FC, GLU construct and GTF (*S. sobrinus*).

Serum IgG antibody to GLU that reacted with GTF enzyme was detected after intranasal (IN) instillation or subcutaneous injection of CVD908FC-GLU. Both *S. typhii* immunizing strains (FC-GLU and control, FC only) were recovered from feces or blood for less than 2 days. Antibody to TT was only detected in animals immunized with the control and GLU-containing strains. The CVD908FC-GLU IN instilled group showed salivary IgA antibody to the GLU. After challenge with cariogenic *S. sobrinus*, 4 of 4 animals immunized with the control *S. typhii* and infected became colonized, whereas only 2 of 6 of the GLU construct immunized animals became colonized. In other experiments, rats were sham immunized (IN) or immunized (IN) with the *Salmonella* control or the *Salmonella* expressing GLU or with GTF/cholera toxin (GTF/CT) alone. *Salmonella* GLU immunization and GTF/CT resulted in significantly reduced recovery of *S. sobrinus* after infection compared to the sham or control immunized groups. Therefore, despite the lack of persistent infection with *Salmonella* in rodents, immunity could be established effectively in serum and secretions, and colonization with cariogenic bacteria was affected.

Example 5

*S. sobrinus* GTF-Polysaccharide Conjugates

Normally, T-cell-independent type 2 polysaccharide (PS) induces low 1° and essentially no 2° immune response. Conjugation of protein to PS results in T cell help for the PS and can significantly increase antibody levels to the protein. Here, GTF was covalently bound, using cyanooxidation, to a water soluble glucan (WSG) product of *S. sobrinus* GTF prepared by the addition of sucrose to *S. sobrinus* GTF. Sprague-Dawley rats (n=6–7/group) were immunized sc, sgv with WSG, GTF, GTF-WSG, tetanus toxoid (TT), TT-WSG, or PBS. All antigens were administered at doses of 1 and 10 μg. Rats were immunized on Day 0 with antigen in complete Fruend's adjuvant (CFA) and on Day 7 in incomplete Fruend's adjuvant (IFA). Blood was collected on Days 21, 35, and 47 (also CLN lymphocytes; day 175) and analyzed for levels of serum IgG antibody to WSG and GTF, and proliferation to GTF.

Conjugation of GTF to WSG resulted in significant elevation of serum IgG to WSG (>100-fold) when compared to unconjugated WSG. In each case, 10 μg of PS antigen provided enhanced response compared to 1 μg. Although no CLN T-cell proliferative responses to the WSG (mean SI=1) were observed, responses to GTF were significantly elevated in both GTF (SI=20) and GTF-WSG (SI=19) groups. Antibody from the GTF-WSG group showed significantly greater inhibition (45%+/−4 vs 17%+/−9) of GTF-mediated incorporation of glucose into WSG. The GTF-WSG conjugate demonstrates increased antibody formation to caries-related antigens and enhanced inhibition of GTF function.

Example 6

Periodontal Bacterial DNA is Suppressive for Immune Response to GTF

CpG motifs have been shown to exhibit adjuvant properties and enhance immune responses. The enhanced immune responses induced by CpG motifs may be mediated through Toll-like receptor 9. Bacterial DNA virtually free of protein was prepared by phenol-chloroform extraction and lipopolysaccharide (LPS) was removed by anion exchange. Seven groups of Rowett rats were immunized with alum alone or with GTF (10 μg/rat) in alum with either no DNA, or *E. coli* DNA, *F. nucleatum* DNA, *P. gingivalis* DNA, active CpG oligonucleotide, or CpG "scramble" oligonucleotide (all 100 µg/rat). The animals were injected in the salivary gland vicinity on Day 0, and bled and salivated on Days 21, 42, and 91, and then given a second injection on Day 105 with the same immunogen administered on Day 0. Animals were sampled 3 and 6 weeks later. Serum IgG antibody to GTF and salivary IgA were analyzed by ELISA.

Animals receiving DNA from either *E. coli, F. nucleatum*, or *P. gingivalis* demonstrated significantly less IgG and IgA antibody than the GTF and alum immunized group. Animals receiving the CpG oligonucleotides had equal or greater antibody than the GTF/alum alone. Rats receiving the scramble oligonucleotide showed less antibody than the CpG oligonucleotide group. Immune responses to the immunizing DNA were not observed in any group. Therefore, DNA from periodontal-associated bacteria does not enhance immune response to antigen of other bacterial species, but in fact suppressed immune responses to GTF. Thus, periodontal bacteria serve to modulate immune responses to injected antigen or to antigen presented by natural routes including local infection.

Equivalents

Those skilled in the art will recognize or be able to ascertain using no more than routine experimentation, many equivalents to the specific embodiments of the invention described herein. Such equivalents are intended to be encompassed in the scope of the following claims.

What is claimed is:

1. An immunogenic composition comprising a biocompatible microparticle and at least one peptide which is an amino acid sequence subunit of glucosyltransferase of 15–22 amino acids in length comprising an amino acid sequence selected from the group consisting of: SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

2. An immunogenic composition comprising a biocompatible microparticle and at least one peptide consisting essentially of SEQ ID NO: 3.

3. An immunogenic composition comprising a biocompatible microparticle and a macromolecular structure, said structure comprising a peptidyl core matrix comprising at least one amino acid selected from the group consisting of a lysine, arginine, and histidine residue; and at least two glucosyltransferase polypeptides covalently attached to said peptidyl core amino acid, wherein said glucosyltransferase polypeptides are selected from the group consisting of SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

4. An immunogenic composition comprising a biocompatible microparticle and a radially branched macromolecular structure, said structure comprising a peptidyl core matrix comprising at least 3 amino acids selected from the group consisting of a lysines, arginine, and histidine residue; and at least 4 glucosyltransferase polypeptides, each polypeptide of which is covalently attached to and radially branched about said peptidyl core amino acid, wherein said glucosyltransferase polypeptides are selected from the group consisting of SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

* * * * *

SEQUENCE LISTING

```
<160> NUMBER OF SEQ ID NOS: 21

<210> SEQ ID NO 1
<211> LENGTH: 21
<212> TYPE: PRT
<213> ORGANISM: Artificial
<220> FEATURE:
<223> OTHER INFORMATION: EAW peptide

<400> SEQUENCE: 1

Ala Asn Asp His Leu Ser Ile Leu Glu Ala Trp Ser Asp Asn Asp Thr
1               5                   10                  15

Pro Tyr Leu His Asp
            20

<210> SEQ ID NO 2
<211> LENGTH: 19
<212> TYPE: PRT
<213> ORGANISM: Artificial
<220> FEATURE:
<223> OTHER INFORMATION: HDS peptide

<400> SEQUENCE: 2

Val Pro Ser Tyr Ser Phe Ile Arg Ala His Asp Ser Glu Val Gln Asp
1               5                   10                  15

Leu Ile Ala

<210> SEQ ID NO 3
<211> LENGTH: 22
<212> TYPE: PRT
<213> ORGANISM: Artificial
<220> FEATURE:
<223> OTHER INFORMATION: GLB peptide

<400> SEQUENCE: 3

Thr Gly Ala Arg Thr Ile Asn Gly Gln Leu Leu Tyr Phe Arg Ala Asn
1               5                   10                  15

Gly Val Gln Val Lys Gly
            20

<210> SEQ ID NO 4
<211> LENGTH: 15
<212> TYPE: PRT
<213> ORGANISM: Artificial
<220> FEATURE:
<223> OTHER INFORMATION: MAC peptide
```

```
<400> SEQUENCE: 4

Pro Gln Trp Asn Gly Glu Ser Glu Lys Pro Tyr Asp Asp His Leu
1               5                   10                  15

<210> SEQ ID NO 5
<211> LENGTH: 15
<212> TYPE: PRT
<213> ORGANISM: Streptococcus mutans

<400> SEQUENCE: 5

Ser Ala Trp Asn Ser Asp Ser Glu Arg Pro Phe Asp Asp His Leu
1               5                   10                  15

<210> SEQ ID NO 6
<211> LENGTH: 15
<212> TYPE: PRT
<213> ORGANISM: Streptococcus mutans

<400> SEQUENCE: 6

Ser Ala Trp Asn Ser Asp Ser Glu Lys Pro Phe Asp Asp His Leu
1               5                   10                  15

<210> SEQ ID NO 7
<211> LENGTH: 15
<212> TYPE: PRT
<213> ORGANISM: Streptococcus mutans

<400> SEQUENCE: 7

Pro Asn Trp Asn Ser Gln Thr Glu Ser Asp Thr Ser Ala Gly Glu
1               5                   10                  15

<210> SEQ ID NO 8
<211> LENGTH: 15
<212> TYPE: PRT
<213> ORGANISM: Streptococcus downei

<400> SEQUENCE: 8

Pro Gln Trp Asn Gly Glu Ser Glu Lys Pro Tyr Asp Asp His Leu
1               5                   10                  15

<210> SEQ ID NO 9
<211> LENGTH: 15
<212> TYPE: PRT
<213> ORGANISM: Streptococcus sobrinus

<400> SEQUENCE: 9

Pro Gln Trp Asn Gly Glu Ser Glu Lys Pro Tyr Asp Asp His Leu
1               5                   10                  15

<210> SEQ ID NO 10
<211> LENGTH: 21
<212> TYPE: PRT
<213> ORGANISM: Streptococcus mutans

<400> SEQUENCE: 10

Ala Asn Asp His Leu Ser Ile Leu Glu Ala Trp Ser Tyr Asn Asp Thr
1               5                   10                  15

Pro Tyr Leu His Asp
            20

<210> SEQ ID NO 11
<211> LENGTH: 21
<212> TYPE: PRT
<213> ORGANISM: Streptococcus mutans
```

-continued

```
<400> SEQUENCE: 11

Ala Ile Asn His Leu Ser Ile Leu Glu Ala Trp Ser Asp Asn Asp Pro
1               5                   10                  15

Gln Tyr Asn Lys Asp
            20

<210> SEQ ID NO 12
<211> LENGTH: 21
<212> TYPE: PRT
<213> ORGANISM: Streptococcus downei

<400> SEQUENCE: 12

Ala Asn Asn His Val Ser Ile Val Glu Ala Trp Ser Asp Asn Asp Thr
1               5                   10                  15

Pro Tyr Leu His Asp
            20

<210> SEQ ID NO 13
<211> LENGTH: 21
<212> TYPE: PRT
<213> ORGANISM: Streptococcus downei

<400> SEQUENCE: 13

Ala Ile Asp His Leu Ser Ile Leu Glu Ala Trp Ser Gly Asn Asp Asn
1               5                   10                  15

Asp Tyr Val Lys Gln
            20

<210> SEQ ID NO 14
<211> LENGTH: 21
<212> TYPE: PRT
<213> ORGANISM: Streptococcus sobrinus

<400> SEQUENCE: 14

Ala Asn Asn His Val Ser Ile Val Glu Ala Trp Ser Asp Asn Asp Thr
1               5                   10                  15

Pro Tyr Leu His Asp
            20

<210> SEQ ID NO 15
<211> LENGTH: 22
<212> TYPE: PRT
<213> ORGANISM: Streptococcus mutans

<400> SEQUENCE: 15

Val Pro Ser Tyr Ser Phe Ile Arg Ala His Asp Ser Glu Val Gln Asp
1               5                   10                  15

Leu Ile Arg Asn Ile Ile
            20

<210> SEQ ID NO 16
<211> LENGTH: 22
<212> TYPE: PRT
<213> ORGANISM: Streptococcus mutans

<400> SEQUENCE: 16

Met Ala Asn Tyr Ile Phe Ile Arg Ala His Asp Ser Glu Val Gln Thr
1               5                   10                  15

Val Ile Ala Lys Ile Ile
            20
```

```
<210> SEQ ID NO 17
<211> LENGTH: 22
<212> TYPE: PRT
<213> ORGANISM: Streptococcus downei

<400> SEQUENCE: 17

Val Pro Ser Tyr Ser Phe Ala Arg Ala His Asp Ser Glu Val Gln Asp
1               5                   10                  15

Leu Ile Arg Asp Ile Ile
            20

<210> SEQ ID NO 18
<211> LENGTH: 22
<212> TYPE: PRT
<213> ORGANISM: Streptococcus downei

<400> SEQUENCE: 18

Val Pro Asn Tyr Val Phe Ile Arg Ala His Asp Ser Glu Val Gln Thr
1               5                   10                  15

Arg Ile Ala Lys Ile Ile
            20

<210> SEQ ID NO 19
<211> LENGTH: 22
<212> TYPE: PRT
<213> ORGANISM: Streptococcus sobrinus

<400> SEQUENCE: 19

Val Pro Ser Tyr Ser Phe Ala Arg Ala His Asp Ser Glu Val Gln Asp
1               5                   10                  15

Ile Ile Arg Asp Ile Ile
            20

<210> SEQ ID NO 20
<211> LENGTH: 19
<212> TYPE: PRT
<213> ORGANISM: Artificial
<220> FEATURE:
<223> OTHER INFORMATION: DGQ peptide

<400> SEQUENCE: 20

Asp Gly Gln Val Gln Tyr Phe Asp Glu Met Gly Tyr Gln Ala Lys Gly
1               5                   10                  15

Lys Phe Val

<210> SEQ ID NO 21
<211> LENGTH: 4
<212> TYPE: PRT
<213> ORGANISM: Artificial
<220> FEATURE:
<223> OTHER INFORMATION: Terminus spacer

<400> SEQUENCE: 21

Cys Ala Gly Ala
1
```